United States Patent [19]

Bruderlein

[11] 4,059,585
[45] Nov. 22, 1977

[54] PROCESS FOR PREPARING AN INTERMEDIATE FOR CNS DEPRESSANTS

[75] Inventor: Francois T. Bruderlein, Montreal, Canada

[73] Assignee: Ayerst McKenna and Harrison Ltd., Montreal, Canada

[21] Appl. No.: 709,144

[22] Filed: July 27, 1976

[51] Int. Cl.$^2$ .......................................... C07D 217/10
[52] U.S. Cl. ............................ 260/286 Q; 260/289 C
[58] Field of Search ......... 260/286 Q, 287 CF, 289 C

[56] References Cited

U.S. PATENT DOCUMENTS 3,657,250  4/1972  Bruderlein et al. .............. 260/286 Q Primary Examiner—Paul M. Coughlan, Jr.
Attorney, Agent, or Firm—Arthur E. Wilfond

[57] ABSTRACT

Disclosed is a process for preparing (4a,13b-trans)-1,2,4,4a,8,9,13b,14-octahydro-3H-benzo[6,7]cyclohepta[1,2,3-de]-pyrido[2,1-a]isoquinolin-3-one involving a 1,3-cycloaddition of a 4-halo-1-butene to 1,7,8,12b-tetrahydrobenzo[1,2]cyclohepta-[3,4,5-de]isoquinoline N-oxide.

9 Claims, No Drawings

PROCESS FOR PREPARING AN INTERMEDIATE FOR CNS DEPRESSANTS

FIELD OF INVENTION

This invention relates to a process for preparing (4a,13b-trans)-1,2,4,4a,8,9,13b,14-octahydro-3H-benzo[6,7]-cyclohepta[1,2,3-de]pyrido[2,1-a]isoquinolin-3-one and to an intermediate used in this process.

PRIOR ART

The object compound of this invention, (4a,13b-trans)-1,2,4,4a,8,9,13b,14-octahydro-3H-benzo[6,7]-cyclohepta[1,2,3-de]-pyrido[2,1-a]isoquinolin-3-one is represented by formula 1

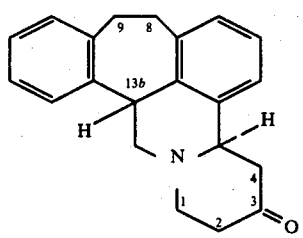

The compound (1) is useful as an intermediate for preparing central nervous system depressants. For example, the compound (1) can be converted to its corresponding ethylenethioketal derivative by reaction with ethanedithiol in the presence of boron trifluoride, followed by desulfurization of the ethylenethioketal derivative with Raney nickel to give (4a,13b-trans)-2,3,4,4a,8,9,13b,14-octahydro-1H-benzo[6,7]cyclohepta[1,2,3-de]pyrido[2,1-a]isoquinoline, a pychotropic agent known generically as taclamine (see F. T. Bruderlein, L. G. Humber and K. Pelz, Can. J. Chem., 52, 2119 (1974).

In addition, the object compound (1) can be transformed to certain 3-substituted benzo[6,7]-cyclohepta[1,2,3-de]pyrido[2,1-a]isoquinolin-3-ols, known to be potent neuroleptic agents, F. T. Bruderlein, L. G. Humber and K. Voith, J. Med. Chem., 18, 185 (1975). For example, the reaction of compound 1 with tertbutyllithium affords (4a,13b-trans)[3(OH),13b(H)-trans]-3-tert-butyl-2,3,4,4a,8,9,13b,14-octahydro-1H-benzo[6,7]-cyclohepta[1,2,3-de]pyrid[2,1-a]isoquinolin-3-ol, known generically as butaclamol, F. T. Bruderlein, L. G. Humber and K. Voith, cited above.

The preparation of the object compound by the addition of methyl vinyl ketone to 1,7,8,12b-tetrahydrobenzo[1,2]-cyclohepta[3,4,5-de]isoquinoline hydrochloride has been described by F. T. Bruderlein, L. G. Humber and K. Pelz, cited above.

One disadvantage of this reported process is that the addition reaction also gives the corresponding 4a,13b-cis isomer of the compound of formula 1, requiring an extra step to separate this cis isomer from the desired 4a,13b-trans-isomer, i.e. the compound of formula 1.

The process of the present invention overcomes the above noted disadvantages by providing a series of facilely executed reactions which lead directly to the desired 4a,13b-trans isomer, i.e., a stereospecific synthesis of the desired isomer.

SUMMARY OF THE INVENTION

The process of this invention is illustrated by the following flow diagram:

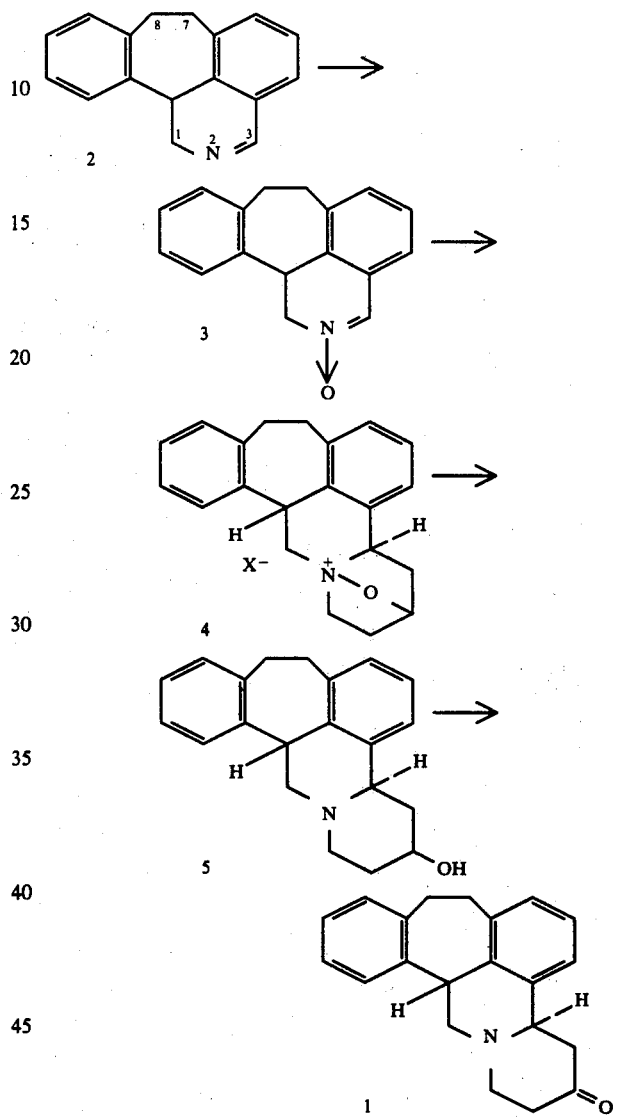

More explicitly, a process for preparing (4a,13b-trans)-1,2,4,4a,8,9,13b,14-octahydro-3H-benzo[6,7]cyclohepta[1,2,3-de]-pyrido[2,1-a]isoquinolin-3-one (1) is provided comprising:

a. oxidizing 1,7,8,12b-tetrahydrobenzo[1,2]cyclohepta[3,4,5-de]-isoquinoline (2) with a peracid to obtain 1,7,8,12b-tetrahydrobenzo[1,2]cyclohepta[3,4,5-de]-isoquinoline N-oxide (3);

b. reacting the last-named compound with a haloolefin of formula

in which X is chloro, bromo or iodo to obtain the corresponding quaternary salt of formula 4

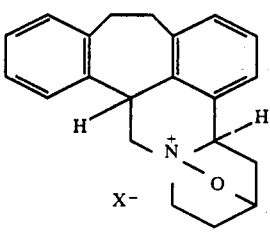

in which X is the same as the halogen of the haloolefin employed;

c. reducing the compound of formula 4 in which X is chloro, bromo or iodo with a complex metal hydride to obtain (4a,13b-trans)-2,3,4,4a,8,9,13b,14-octahydro-1H-benzo[6,7]isoquinolin-3-ol; and d. oxidizing the last named compound with a reagent for converting a hydroxy function to the corresponding keto function to obtain the desired compound of formula 1.

DETAILS OF THE INVENTION

With reference to the flow diagram, the starting material of formula 2, 1,7,8,12b-tetrahydrobenzo[1,2]cyclohepta[3,4,5-de]isoquinoline, has been described by L. G. Humber et al., J. Heterocyclic Chem., 3,247 (1966).

In the first step of the process the starting material of formula 2 is oxidized with a peracid, for example, hydrogen peroxide, or preferably an organic peracid. for instance, m-chloroperbenzoic acid, perbenzoic acid or peracetic acid, to give the corresponding N-oxide of formula 3. Any practical solvent inert to the reaction conditions can be employed; acetic acid is a convenient solvent when hydrogen peroxide or peracetic acid is employed, chloroform is quite suitable when m-chloroperbenzoic acid or perbenzoic acid is employed. Preferred ranges for the the reaction time and temperature are from 15 minutes to 24 hours and 10° to 40° C, respectively.

In the second step the corresponding N-oxide of formula 3 is reacted with a haloolefin of formula

in which X is chloro, bromo or iodo to give the corresponding quaternary salt of formula 4 in which X is the same as the halogen atom of the haloolefin employed. This reaction is conveniently performed in an aprotic solvent, for example, benzene, tetrahydrofuran or dioxane. Convenient reaction time and temperatures usually range from six to 24 hours at 60° to 100° C.

In the third step the quaternary salt of formula 4 in which X is chloro, bromo or iodo is reduced with a complex metal hydride to yield the aminoalcohol of formula 5. Examples of complex metal hydrides suitable for this purpose are lithium aluminum hydride, sodium borohydride, lithium aluminum hydride-aluminum chloride and diborane. Lithium aluminium hydride and sodium borohydride are preferred reducing agents. The reduction is usually effected at 10° - 30° C, preferably at room temperature.

Subsequent oxidation of the aminoalcohol of formula 5 with a reagent for converting a hydroxy function to the corresponding keto function yields the corresponding aminoketone of formula 1. Suitable oxidizing agents include sodium dichromate, chromium trioxidepyridine complex or chromium trioxide-sulfuric acid, with the former being preferred. In this manner the aminoketone of formula 1 is obtained, the aminoketone being identical to (4a,13b-trans)1,2,4,4a-8,9,13b,14-octahydro-3H-benzo[6,7]cyclohepta[1,2,3-de]pyrido[2,1-a]isoquinolin-3-one, described by F. T. Bruderlein et al., Can. J. Chem., 52, 2119 (1974); see also F. T. Bruderlein et al., J. Med. Chem., 18, 185 (1975).

The following examples illustrate further this invention.

EXAMPLE 1

1,7,8,12b-tetrahydrobenzo[1,2]-cyclohepta[3,4,5-de]-Isoquinoline N-oxide (3)

To a cold solution (5° - 15° C) of 1,7,8,12b-tetrahydrobenzo[1,2]-cyclohepta[3,4,5-de]isoquinoline (2.7 g) in chloroform (30 ml), a solution of m-chloroperbenzoic acid (2.3 g) in 20 ml of chloroform is added dropwise. The reaction mixture is allowed to stand at room temperature (i.e., 20° - 25° C) for 30 minutes. The reaction mixture is then washed with 15% ammonium hydroxide and water. The reaction mixture is dried (MgSO₄) and concentrated to yield an oily residue. The oily residue is crystallized from benzene/hexane to give the title compound, mp 156° - 158° C.

EXAMPLE 2

(4a,13b-trans)-2,3,4,4a,8,9,13b,14-Octahydro-1H-benzo[6,7]cyclohepta[1,2,3-de]pyrido[2,1-a]isoquinoline-3-ol (5)

A mixture of 1,7,8,12b-tetrahydrobenzo[1,2]cyclohepta3,4,5-de]iso quinoline N-oxide (8.0 g, described in Example 1) and the compound of formula

4-bromo-1-butene (5.3 ml), in benzene (105 ml) is stirred and heated at reflux for 18 hours. After cooling the resulting precipitate is collected to give 3,15-epoxy-2,3,4,4a,8,9,13b,14-octahydro-1H-benzo[6,7]cyclohepta[1,2,3-de]-pyrido[2,1-a]isoquinoline hydrobromide (4; X = Br), mp 158° C.

The latter compound (4.3 g) is reduced with 1.0 g of lithium aluminum hydride in tetrahydrofuran (60 ml) at room temperature. Work up of the reaction mixture gives an oil, which is subjected to chromatography on silica gel. Elution with increasing amounts of chloroform in benzene and concentration of the eluant gives the title compound, 157°-159° C.

The corresponding hydrochloric acid addition salt of the latter compound has mp 288° - 290° C, after recrystallization from ethanol/diethyl ether.

The title compound obtained by way of this Example is identical to the compound described as 1,4,5,6,6a,10,11,15b-octahydro-3H-benzo[6,7]cyclohepta[1,2,3-de]pyrido[2,1-a]isoquinolin-5ol, isomer A, described by F. T. Bruderlein and L. G. Humber in U.S. Pat. No. 3,657,250, issued Apr. 18, 1972.

By replacing lithium aluminum hydride with an equivalent amount of sodium borohydride in the procedure of this example, the title compound also is obtained.

EXAMPLE 3

1,2,4,4a,8,9,13b,14-Octahydro-3H-benzo[6,7]cyclohepta[1,2,3-de]pyrido[2,1-a]isoquinolin-3-one (1)

A solution of sodium dichromate (3.0 g) in conc. sulfuric acid (3 ml) and water (6 ml) is added dropwise to a solution of (4a,13b-trans)-2,3,4,4a,8,9,13b,14-octahydro-1H-benzo[6,7]cyclohepta[1,2,3-de]-pyrido[2,1-a]isoquinolin-3ol (3.0 g, described in Example 2) while maintaining the temperature of the reaction mixture below 80° C. After the addition the reaction mixture is stirred for 10 minutes and then poured into water. The mixture is rendered basic with dilute sodium bicarbonate and extracted with diethyl ether. The extract is concentrated and the resulting residue is crystallized from isopropanol to give the title compound, mp 163° – 165° C, identical to the compound of the same name described by F. T. Bruderlein, L. G. Humber and K. Pelz, Can. J. Chem., 52, 2119 (1974).

I claim:

1. A process for preparing (4a,13b-trans)-1,2,4,4a,8,9,13b,14-octahydro-3H-benzo[6,7]cyclohepta[1,2,3-de]pyrido[2,1-a]isoquinolin-3-one, comprising:
    a. oxidizing 1,7,8,12b-tetrahydrobenzo[1,2]cyclohepta[3,4,5-de]-isoquinoline with a peracid oxidizing agent to obtain 1,7,8,12b-tetrahydrobenzo[1,2]cyclohepta[3,4,5-de]isoquinoline N-oxide;
    b. reacting the last-named compound with a haloolefin of formula

in which X is chloro, bromo or iodo to obtain the corresponding quaternary salt of formula 4

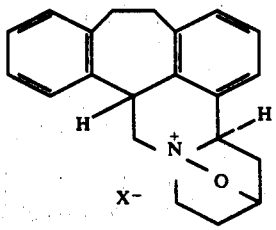

in which X is the same as the halogen of the haloolefin employed;
    c. reducing the compound of formula 4 in which X is chloro, bromo or iodo with a complex metal hydride reducing agent to obtain (4a,13b-trans)-2,3,4,4a,8,9,13b,14-octahydro-1H-benzo[6,7]-isoquinolin-3-ol; and
    d. oxidizing the last-named compound with a reagent for converting a hydroxy function to the corresponding keto function to obtain (4a,13b-trans)-1,2,4,4a,8,9,13b,14-octahydro-3H-benzo[6,7]cyclohepta[1,2,3-de]pyrido[2,1-a]isoquinolin-3-one.

2. The process of claim 1 in which the peracid is hydrogen peroxide.

3. The process of claim 1 in which the peracid is m-perchloroperbenzoic acid, perbenzoic acid or peracetic acid.

4. The process of claim 1 in which the haloolefin is 4-bromo-1-butene.

5. The process of claim 1 in which the complex metal hydride reducing agent is lithium aluminum hydride or sodium borohydride.

6. The process of claim 1 in which the reagent for converting a hydroxy function to the corresponding keto function is sodium dichromate, chromium trioxide-pyridine complex, or chromium trioxide-sulfuric acid.

7. The process of claim 1 in which the peracid oxidizing agent is m-chloroperbenzoic acid, the haloolefin is 4-bromo-1-butene, the complex metal hydride is lithium aluminum hydride, and the reagent for converting a hydroxy function to the corresponding keto function is sodium dichromate.

8. A compound of the formula

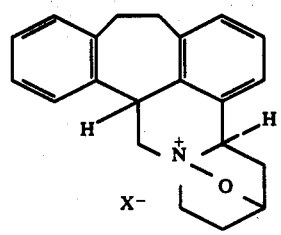

in which X is chloro, bromo or iodo.

9. 3,15-Epoxy-2,3,4,4a,8,9,13b,14-octahydro-1H-benzo[6,7]cyclohepta[1,2,3-de]pyrido[2,1-a]isoquinoline hydrobromide, as claimed in claim 8.

* * * * *

UNITED STATES PATENT AND TRADEMARK OFFICE
CERTIFICATE OF CORRECTION

PATENT NO. : 4,059,585
DATED : November 22, 1977
INVENTOR(S) : Francois T. Bruderlein It is certified that error appears in the above-identified patent and that said Letters Patent are hereby corrected as shown below:

Claim 3, line 2, "m-perchloroperbenzoic acid" should be read — m-chloroperbenzoic acid —.

Signed and Sealed this

Thirtieth Day of May 1978

[SEAL]

Attest:

RUTH C. MASON
Attesting Officer

LUTRELLE F. PARKER
Acting Commissioner of Patents and Trademarks